(12) United States Patent
Bowman (10) Patent No.: US 10,342,708 B2
(45) Date of Patent: Jul. 9, 2019

(54) DECORATIVE BANDAGE AND CORRESPONDING SYSTEMS AND METHODS

(71) Applicant: Medline Industries, Inc., Mundelein, IL (US)

(72) Inventor: Michael Bowman, Chicago, IL (US)

(73) Assignee: Medline Industries, Inc., Northfield, IL (US)

( * ) Notice: Subject to any disclaimer, the term of this patent is extended or adjusted under 35 U.S.C. 154(b) by 1084 days.

(21) Appl. No.: 14/216,484

(22) Filed: Mar. 17, 2014

(65) Prior Publication Data

US 2015/0257935 A1    Sep. 17, 2015

(51) Int. Cl.
  *A61F 13/00* (2006.01)
  *A61F 13/02* (2006.01)

(52) U.S. Cl.
  CPC .... *A61F 13/00059* (2013.01); *A61F 13/0226* (2013.01); *A61F 2013/00153* (2013.01)

(58) Field of Classification Search
  CPC ............ A61F 13/00059; A61F 13/0226; A61F 13/00051; A61F 13/00; A61F 13/02; A61F 13/0206; A61F 2013/00153; A61F 2013/00089
  USPC ..................................................... D24/189
  See application file for complete search history.

(56) References Cited

U.S. PATENT DOCUMENTS

| | | | |
|---|---|---|---|
| 4,867,150 A * | 9/1989 | Gilbert | A61F 13/0206 428/425.1 |
| 6,150,609 A * | 11/2000 | Baldwin | H02G 3/14 174/66 |
| 6,455,752 B1 | 9/2002 | Vesey | |
| 6,512,160 B1 | 1/2003 | Rutsky | |
| 6,924,411 B2 | 8/2005 | Reider | |
| 7,988,742 B2 | 8/2011 | Stein et al. | |
| 2002/0040202 A1* | 4/2002 | Levin | A61F 13/0203 602/43 |
| 2004/0246106 A1* | 12/2004 | Kain | G04G 11/00 340/309.16 |
| 2006/0229540 A1 | 10/2006 | Atwood | |
| 2007/0010776 A1 | 1/2007 | Price | |
| 2013/0046261 A1 | 2/2013 | Reif | |
| 2013/0131565 A1 | 5/2013 | Dallafior | |
| 2015/0239614 A1* | 8/2015 | Aeri | B65D 25/205 40/665 |

\* cited by examiner

Primary Examiner — Victoria J Hicks
(74) Attorney, Agent, or Firm — Philip H. Burrus, IV (57) ABSTRACT

A decorative bandage (800) is provided. The decorative bandage can include a backing layer (100) defining a first major face (101) and a second major face (301). An adhesive (302) can be disposed along one of the first major face or the second major face. A pad (303) can be disposed along the adhesive layer. Another of the first major face or the second major face can include one or more design elements (601) defining a writing surface appearance (901), such as that of a blackboard or a whiteboard. A decorative bandage accessory (1300), such as one or more sticker sets 1301,1302, can be included so that a user can customize the decorative bandage.

12 Claims, 7 Drawing Sheets

FIG. 16

DECORATIVE BANDAGE AND CORRESPONDING SYSTEMS AND METHODS

BACKGROUND

Technical Field

This disclosure relates generally to wound care devices, and more particularly to bandages and bandage methods.

Background Art

Bandages are used as wound dressings. Placing a bandage over a wound provides a barrier for the wound that prevents the entry of microbes, contaminants, and debris. The wound beneath the bandage can then heal rapidly with reduced risk of secondary infection.

Traditional bandages had a singular appearance—they were roughly skin-toned strips that came in a single, brownish color. Such bandages are relatively uninteresting to users. This can lead to less bandage use, which in turn can result in delayed healing times or increased infection. Moreover, fashion conscious patients may eschew such bandages because they are plain and uninteresting. It would be advantageous to have a more interesting bandage.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the disclosure provide a decorative bandage that is interesting in appearance, thereby making users more likely to utilize a bandage to cover a wound during the healing process. In one embodiment, the decorative bandage comprises design elements to have a blackboard, whiteboard, or other writing surface appearance. Accessory devices, such as stickers with letters disposed thereon, can be adhered to the blackboard, whiteboard, or other writing surface appearance to customize the decorative bandage. Embodiments of the disclosure are especially interesting to children, and can provide a distraction from the wound that allows the wound to heal more quickly. Embodiments of the disclosure also provide an interesting activity for the patient to enjoy while the wound heals. Moreover, the incentive of receiving such a bandage from a doctor, nurse, or healthcare provider may can make a patient more willing to undergo wound treatment.

In one embodiment, a decorative bandage includes a backing layer and a pad. The backing layer can define a first major face and a second major face. Adhesive can be disposed along one of the first major face or the second major face. The pad can also be disposed along the one of the first major face or the second major face.

In one embodiment, on the other of the first major face or the second major face is disposed one or more decorative elements. These decorative elements can be printed on the backing layer, vapor deposited on the backing layer, molded into the backing layer, or otherwise integrated with the backing layer. In one or more embodiments, the one or more design elements define a writing surface appearance. Examples of writing surface appearances include a blackboard appearance or a whiteboard appearance. For instance, where the writing surface appearance comprises a blackboard appearance, the blackboard appearance can include a black or grey plane inscribed within a border. The border can define a wood frame or metal frame appearance. Similarly, where the writing surface appearance comprises a whiteboard appearance, the whiteboard appearance, the whiteboard appearance can comprise a white, off-white, light grey, or colored plane inscribed within a border. The border can define a metal frame appearance, a plastic frame appearance, or in some cases a wood frame appearance.

In one or more embodiments, other design instruments can be disposed on the backing layer. For example, in one embodiment a writing instrument appearance can be disposed on the writing surface appearance. Where the writing surface appearance is a blackboard appearance, the writing instrument appearance can be a chalk stick appearance. Where the writing surface appearance is a whiteboard appearance, the writing instrument appearance can be an ink pen appearance of marker appearance. Other design elements, such as eraser appearances, writing appearances, and so forth can also be included.

In one or more embodiments, a system includes a decorative bandage and one or more accessories. In one embodiment, the accessories comprise a plurality of stickers. Each sticker can include a letter, number, symbol, person, fanciful character, or other decorative element. A user can then selectively remove stickers to spell words, create numbers, tell stories, make cartoons, and so forth. They can customize their decorative bandage via the placement of stickers in one or more embodiments.

Advantageously, a system including a decorative bandage and a plurality of stickers provides not only a distraction for patients undergoing wound care, but an incentive to begin wound care as well. Illustrating by example, a young patient may be reluctant to undergo would care because such care may sting, hurt, or otherwise be uncomfortable. However, if a doctor offers a system configured in accordance with one or more embodiments of the disclosure to such a patient, the thought of receiving the system—it being so attractively enticing—may incentivize the patient to allow the wound to be treated. Additionally, the system provides a distractive "customization game" from the wound that helps allow the wound to heal since the user is so busy customizing the decorative bandage that they do not manipulate or otherwise disturb the wound. Finally, users are more apt to actually use bandages during wound care when those bandages are fashionably chic as are embodiments of the present disclosure.

Figure 1:
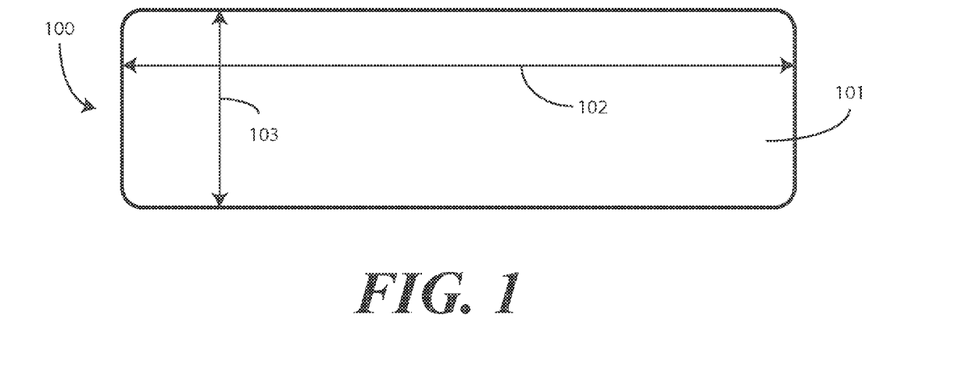
FIG. 1 illustrates one explanatory backing layer in accordance with one or more embodiments of the disclosure.

Turning now to FIG. 1, illustrated therein in is a backing layer 100 configured in accordance with one or more embodiments of the disclosure. The backing layer 100 of FIG. 1 defines a first major face 101 and a second major face, disposed on a side of the backing layer 100 opposite to the first major face 101. The second major face will be shown in more detail with reference to FIG. 3 below.

In one embodiment, the backing layer 100 is opaque. In another embodiment, the backing layer 100 pellucid. Where the backing layer 100 is opaque, it can be manufactured from a colored material in one or more embodiments.

In one embodiment, the backing layer 100 is manufactured from a thermoplastic material. In other embodiments, different materials can be used. The backing layer 100 can be manufactured from various materials or fabrics suitable for use in bandage applications.

In one or more embodiments, the backing layer 100 is manufactured from a material that supports ink or other pigment printing process to carry design elements disposed on one of the first major face 101 or the second major face. In one embodiment, the backing layer 100 and is pliant and at least slightly stretchable. In other embodiments, the backing layer 100 can be semi-flexible and/or rigid.

While the backing layer 100 of FIG. 1 is generally rectangular with rounded corners, it will be obvious to those of ordinary skill in the art having the benefit of this disclosure that the backing layer can take other shapes as well. For example, in on embodiment the backing layer 100 is rectangular. In other embodiments the backing layer 100 can be shaped to accommodate a particular need or application. The backing layer 100 can be cut or shaped into any number of design shapes, silhouette shapes, or other desired shapes.

In one embodiment, a length 102 of the backing layer 100 is between three and four inches, inclusive. In one embodiment, a width 103 of the backing layer 100 is between one and two inches, inclusive. Other dimensions will be obvious to those of ordinary skill in the art having the benefit of this disclosure.

Figure 2:
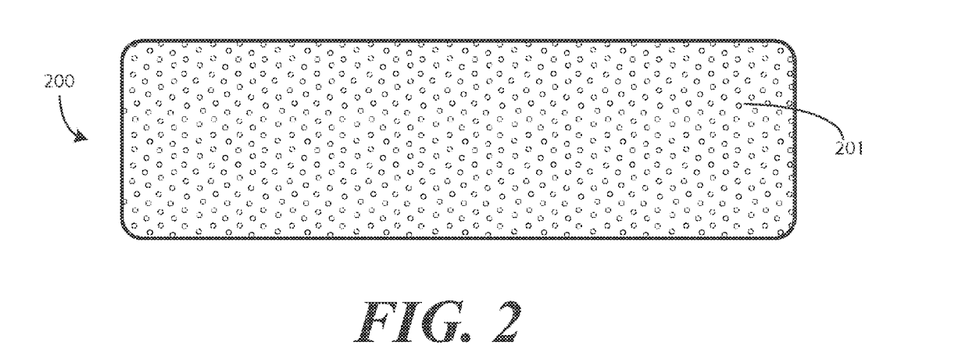
FIG. 2 illustrates another explanatory backing layer in accordance with one or more embodiments of the disclosure.

Turning now to FIG. 2, illustrated therein is another backing layer 200 suitable for use with one or more embodiments of the disclosure. The backing layer 200 of FIG. 2, like the backing layer (100) of FIG. 1, defines a first major face 201 and a second major face. The second major face is disposed on a side of the backing layer 200 opposite to the first major face 201. The backing layer 200 can be manufactured from a thermoplastic material that is pliant and at least slightly stretchable.

In the illustrative embodiment of FIG. 2, the backing layer 200 is perforated. This allows air to pass from a side adjacent to the first major face 201 to the opposite side adjacent to the second major face. Perforating the backing layer 200 allows ambient air to reach a wound, which is some cases, can result in faster healing.

Figure 3:
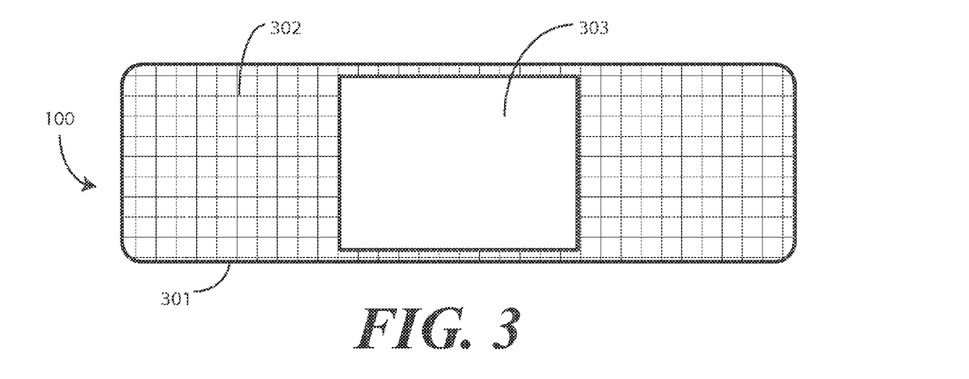
FIG. 3 illustrates a bottom plan view of one explanatory bandage configured in accordance with one or more embodiments of the disclosure.

Turning now to FIG. 3, illustrated therein is the backing layer 100 of FIG. 1. In FIG. 3, the second major face 301 is shown. In one embodiment, the second major face has an adhesive 302 and a pad 303 disposed thereon.

The adhesive 302 can be rolled, sprayed, vapor deposited, or otherwise deposited on the second major face 301 of the backing layer 100. The adhesive 302 can be initially placed on the backing layer 100. The pad 303 can then be placed along the adhesive 302. In this illustrative embodiment, the pad 303 is placed centrally along the backing layer 100. In one embodiment, the adhesive 302 comprises a pressure sensitive adhesive. Other types of adhesive will be obvious to those of ordinary skill having the benefit of this disclosure.

In one embodiment, the pad 303 comprises an absorbent pad. For example, the absorbent pad can be manufactured from gauze or other similar material. The pad 303 can be manufactured from a patterned weave or layering in one or more embodiments. In other embodiments the pad 303 can be a non-absorbent pad that is hydrophobic. Other types of pads will be obvious to those of ordinary skill in the art having the benefit of this disclosure.

Figure 4:
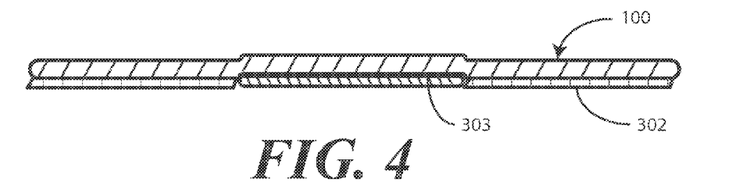
FIG. 4 illustrates a sectional side elevation view of one explanatory bandage configured in accordance with one or more embodiments of the disclosure.
Figure 5:
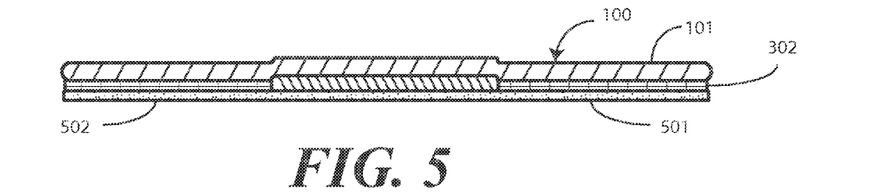
FIG. 5 illustrates another sectional side elevation view of another explanatory bandage configured in accordance with one or more embodiments of the disclosure.

Turning now to FIG. 4, illustrated therein is a sectional side elevation view of the assembly of FIG. 3. As shown, the backing layer 100 carries the adhesive 302 and the pad 303. As shown in FIG. 5, one or more releasable strips 501,502 can be attached to the adhesive 302 so as to prevent the adhesive 302 from sticking to anything prior to usage. A user can remove the releasable strips 501,502 to expose the adhesive 302. The user can then place the pad 303 over a wound and press the first major face 101 of the backing layer to apply the assembly to a wound.

Figure 6:
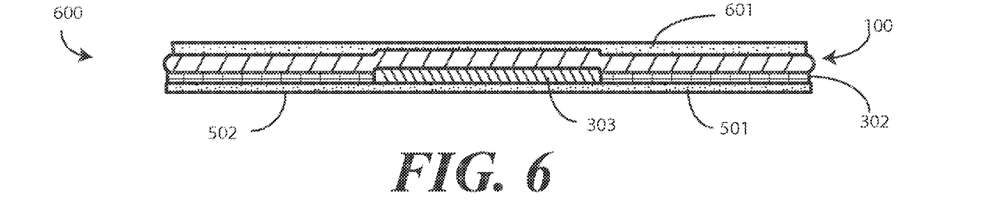
FIG. 6 illustrates another sectional side elevation view of an explanatory decorative bandage configured in accordance with one or more embodiments of the disclosure.

Turning now to FIG. 6, illustrated therein is a sectional side elevation view of a decorative bandage 600 in accordance with one or more embodiments of the disclosure. The decorative bandage 600 includes a backing layer 100, the adhesive 302 and the pad 303. The decorative bandage 600 can optionally include the releasable strips 501,502 as well.

In one or more embodiments, a major face disposed opposite the backing layer 100 from the adhesive carries one or more design elements 601. The design elements 601 can provide a form of decoration, graphic, image, or other ornamentation along a major face of the backing layer 100. While the design elements 601 can take many forms, in one or more embodiments of the disclosure the design elements 601 comprise a writing surface appearance. This will be shown in more detail with reference to FIGS. 8-12 below.

The design elements 601 can be disposed along the major face of the backing layer 100 by depositing colorants via a printing process or by other techniques. For example, the design elements 601 can comprises a printable material that is suitable for deposition along the backing layer from a printer, such as an ink jet printer, laser printer, or other type of printer, to form graphic images along the backing layer 100. The design elements 601 can be constructed from a covering disposed along a major face of the backing layer 100 as well. The design elements 601 can be deposited along all of the major face of the backing layer 100 in one embodiment. Alternatively, the design elements 601 can be selectively deposited only along portions of the major face of the backing layer 100.

Figure 7:
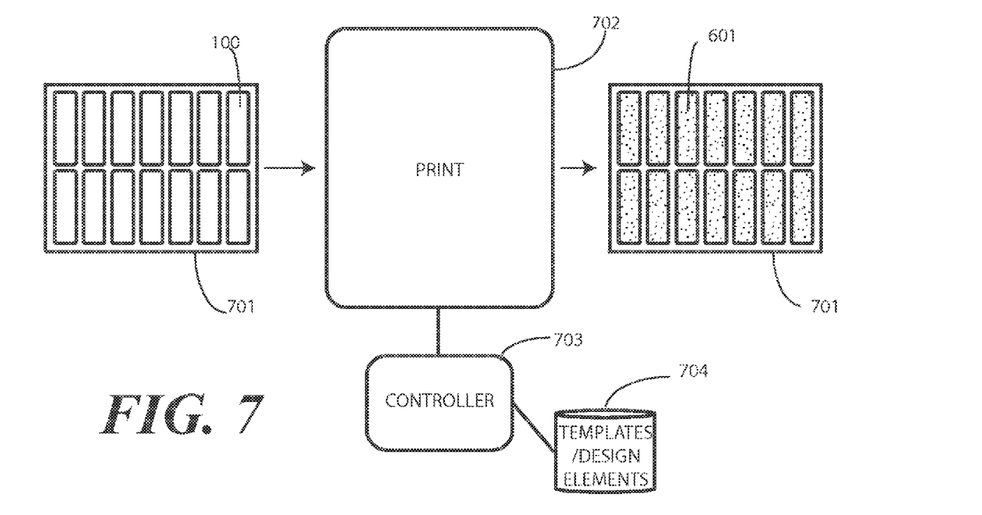
FIG. 7 illustrates an explanatory method and system in accordance with one or more embodiments of the disclosure.

Turning now to FIG. 7, illustrated therein is a method for disposing the design elements 601 on the backing layer 100 in accordance with one or more embodiments of the disclosure. As shown in FIG. 7, a plurality of backing layers can be configured in a sheet 701 with each backing layer separable from another via perforations disposed along perimeters of the backing layers.

The sheet 701 can be fed into a printer 702 that is operable with a controller 703 and a database 704 that stores templates and/or design elements. The controller 703, which can be a computer, processor, or other circuitry, retrieves the templates and/or design elements from the database 704 and applies them to the backing layers via the printer 702. In one embodiment, the printer 702 is an ink jet printer and the design elements 601 comprise ink that is deposited along each backing layer 100. However, other types of printers suitable for depositing the design elements 601 on the backing layer 100 will be obvious to those of ordinary skill in the art having the benefit of this disclosure. Once the design elements 601 are created, the printer 702 ejects the sheet 701 for assembly and packaging.

Figure 8:
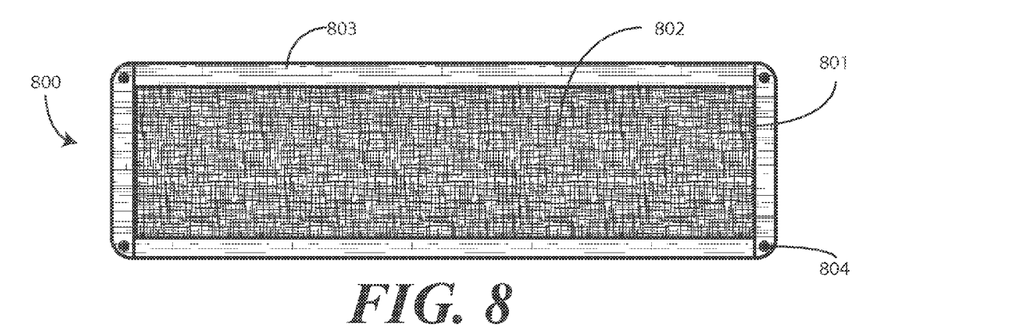
FIG. 8 illustrates a top plan view of one explanatory decorative bandage in accordance with one or more embodiments of the disclosure.

Turning now to FIG. 8, illustrated therein is one explanatory decorative bandage 800 configured in accordance with one or more embodiments of the disclosure. In this illustrative embodiment, the design elements (601) of the decorative bandage 800 define a writing surface appearance, and more particularly, a blackboard appearance 801. Said differently, the upper major face of the decorative bandage 800 looks to a viewer like a blackboard.

In this illustrative embodiment, the blackboard appearance 801 comprises appearance comprising a black plane 802. The black plane 802 could alternatively be a green pane or a grey pane, as many blackboards employ such colors on their writing surfaces. In yet another embodiment, a blue plane can be substituted for the black plane 802. Other colors will be obvious to those of ordinary skill having the benefit of this disclosure.

In the illustrative embodiment of FIG. 8, the black plane 802 is inscribed within a border defining a wood frame appearance 803. The wood frame appearance 803 of FIG. 8 comprises four wood boundary components and optional peg couplings 804. Other wood frame appearances will be obvious to those of ordinary skill in the art having the benefit of this disclosure. For example, rather than using four wood boundary components, the wood frame appearance 803 could be a single, continuous wood boundary component. Similarly, a metal frame appearance could be substituted for the wood frame appearance 803 of FIG. 8.

Figure 9:
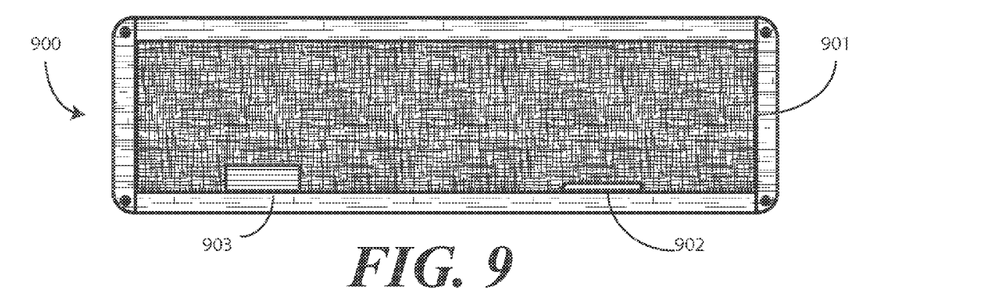
FIG. 9 illustrates another top plan view of another explanatory decorative bandage in accordance with one or more embodiments of the disclosure.

The writing surface appearance can further comprise other design elements. For example, turning to FIG. 9, illustrated therein is another decorative bandage 900 having a writing surface appearance 901. The writing surface appearance 901 of FIG. 9 comprises another design element 902 defining a writing instrument appearance. The writing instrument appearance is disposed along the writing surface appearance 901, which in this embodiment is a blackboard appearance. In this embodiment, the writing instrument appearance comprises a chalk stick appearance. Other writing instrument appearances will be obvious to those of ordinary skill in the art having the benefit of this disclosure. The writing surface appearance 901 can include additional decorative elements as well. For example, in one embodiment, the writing surface appearance 901 also includes an eraser appearance 903.

Figure 10:
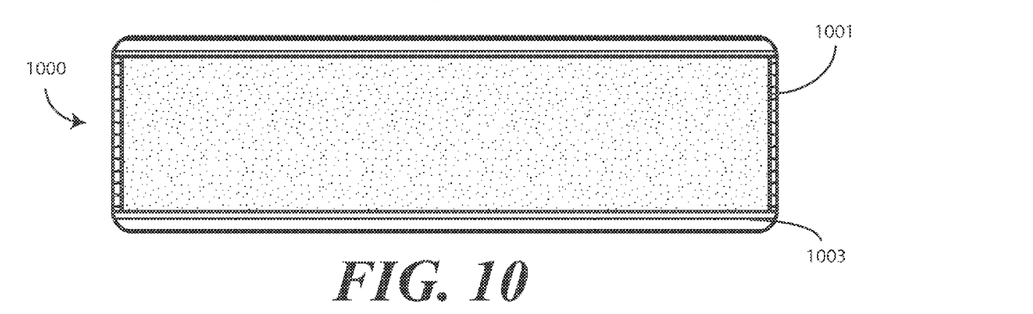
FIG. 10 illustrates another top plan view of another explanatory decorative bandage in accordance with one or more embodiments of the disclosure.

While a blackboard appearance is one example of a writing surface appearance 901, embodiments of the disclosure are not so limited. Turning now to FIG. 10, illustrated therein is one explanatory decorative bandage 1000 configured in accordance with one or more embodiments of the disclosure. In this illustrative embodiment, the design elements (601) of the decorative bandage 1000 define a writing surface appearance that is a whiteboard appearance 1001. Said differently, the upper major face of the decorative bandage 1000 looks to a viewer like a whiteboard.

In this illustrative embodiment, the whiteboard appearance 1001 comprises appearance comprising a white plane 1002. The white plane 1002 could alternatively be off-white, light grey, or other colored plane that resembles a dry-erase board.

In the illustrative embodiment of FIG. 8, the white plane 1002 is inscribed within a border defining a metal frame appearance 1003. The metal frame appearance 1003 of FIG. 10 comprises four metal boundary components. Other metal frame appearances will be obvious to those of ordinary skill in the art having the benefit of this disclosure. For example, rather than using four metal boundary components, the metal frame appearance 1003 could be a single, continuous metal boundary component. Similarly, a plastic or wood frame appearance could be substituted for the metal frame appearance 1003 of FIG. 10.

Figure 11:
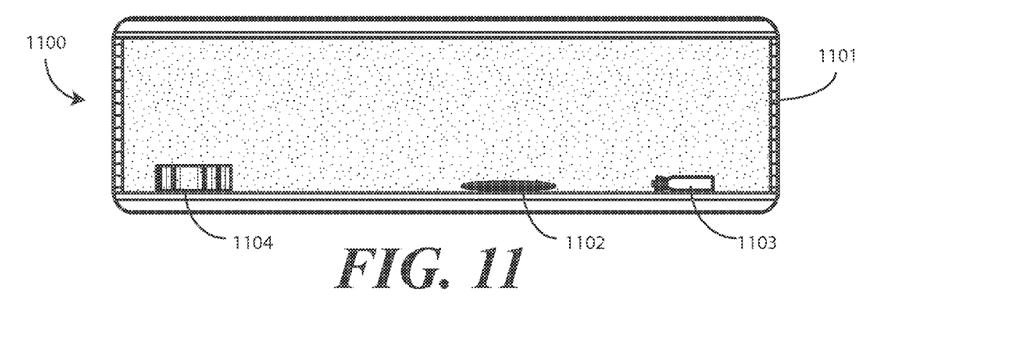
FIG. 11 illustrates another top plan view of another explanatory decorative bandage in accordance with one or more embodiments of the disclosure.

The writing surface appearance can further comprise other design elements. For example, turning to FIG. 11, illustrated therein is another decorative bandage 1100 having a writing surface appearance 1101. The writing surface appearance 1101 of FIG. 11 comprises another design element defining a writing instrument appearance. The writing instrument appearance is disposed along the writing surface appearance 1101, which in this embodiment is a whiteboard appearance. In this embodiment, the writing instrument appearance comprises one of an ink pen appearance 1102, a marker appearance 1103, or combinations thereof. Other writing instrument appearances will be obvious to those of ordinary skill in the art having the benefit of this disclosure. The writing surface appearance 1101 can include additional decorative elements as well. For example, in one embodiment, the writing surface appearance 1101 also includes an eraser appearance 1104.

Figure 12:
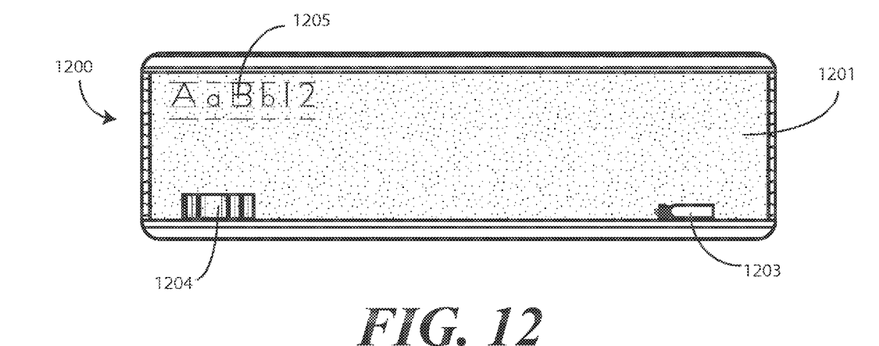
FIG. 12 illustrates another top plan view of another explanatory decorative bandage in accordance with one or more embodiments of the disclosure.

Any of a number of other decorative elements can be added to decorative bandages without departing from the spirit and scope of the disclosure. To provide just one of the many examples of decorative elements that can be used, turning now to FIG. 12 illustrated therein is yet another decorative bandage 1200 in accordance with embodiments of the disclosure. In FIG. 12 a writing surface appearance 1201 is configured as a dry-erase marker appearance. The writing surface appearance 1201 includes a marker appearance 1203 and an eraser appearance 1204.

Additionally, this illustrative embodiment includes a script appearance 1205 as well. The script appearance 1205 can include letters, symbols, characters, numbers, or combinations thereof. In this embodiment, the script appearance 1205 comprises letters and numbers that appear to have been written on a dry-erase board with a dry-erase marker. Note that the script appearance can be applied to other writing surface appearances as well. For example, when applied to a blackboard appearance, the script appearance can look like objects drawn with a piece of chalk on a blackboard.

Figure 13:
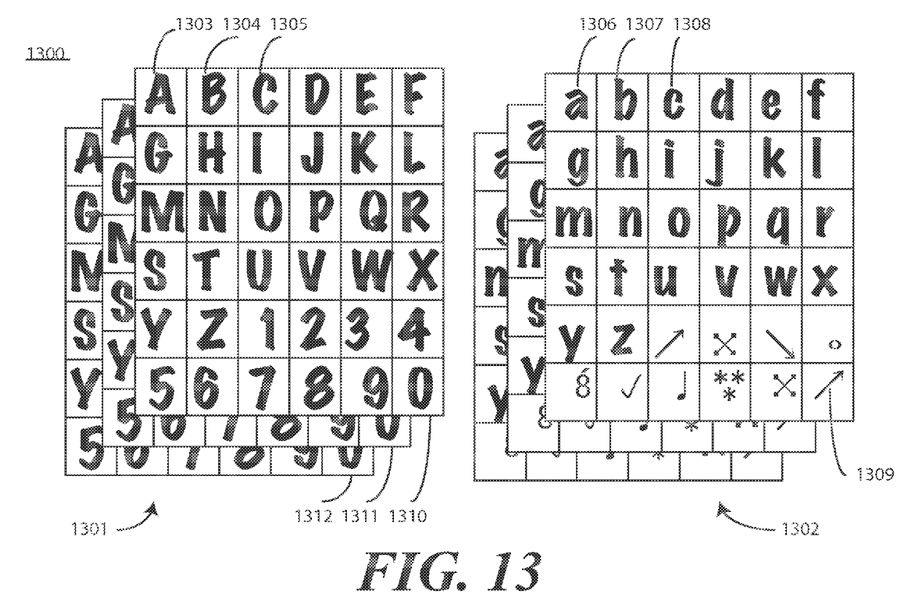
FIG. 13 illustrates an explanatory decorative bandage accessory in accordance with one or more embodiments of the disclosure.

Turning now to FIG. 13, illustrated therein is one embodiment of a decorative bandage accessory 1300 in accordance with one or more embodiments of the disclosure. The decorative bandage accessory 1300 is configured as one or more sticker sets 1301,1302. Each sticker set 1301,1302 includes a plurality of stickers 1303,1304,1305,1306,1307,1308,1309. Each sticker 1303,1304,1305,1306,1307,1308,1309 includes an adhesive backing to adhere to a writing surface appearance of a decorative bandage configured in accordance with one or more embodiments of the disclosure.

Each sticker 1303,1304,1305,1306,1307,1308,1309 can include a letter, a symbol, a character, a graphical representation, or a number on a side opposite the adhesive backing. For example, sticker 1303 includes a capital letter. Sticker 1306 includes a lower case letter. Sticker 1309 includes a symbol and so forth.

In the illustrative embodiment of FIG. 13, sticker set 1301 includes the letters A-Z and the numbers one through nine and zero disposed thereon. Sticker set 1301 includes a plurality of sheets 1310,1311,1312 so that any given number or letter can be replicated when attaching the stickers 1303,1304,1305,1306,1307,1308,1309 to the writing surface appearances of decorative bandages in accordance with embodiments of the disclosure.

Figure 14:
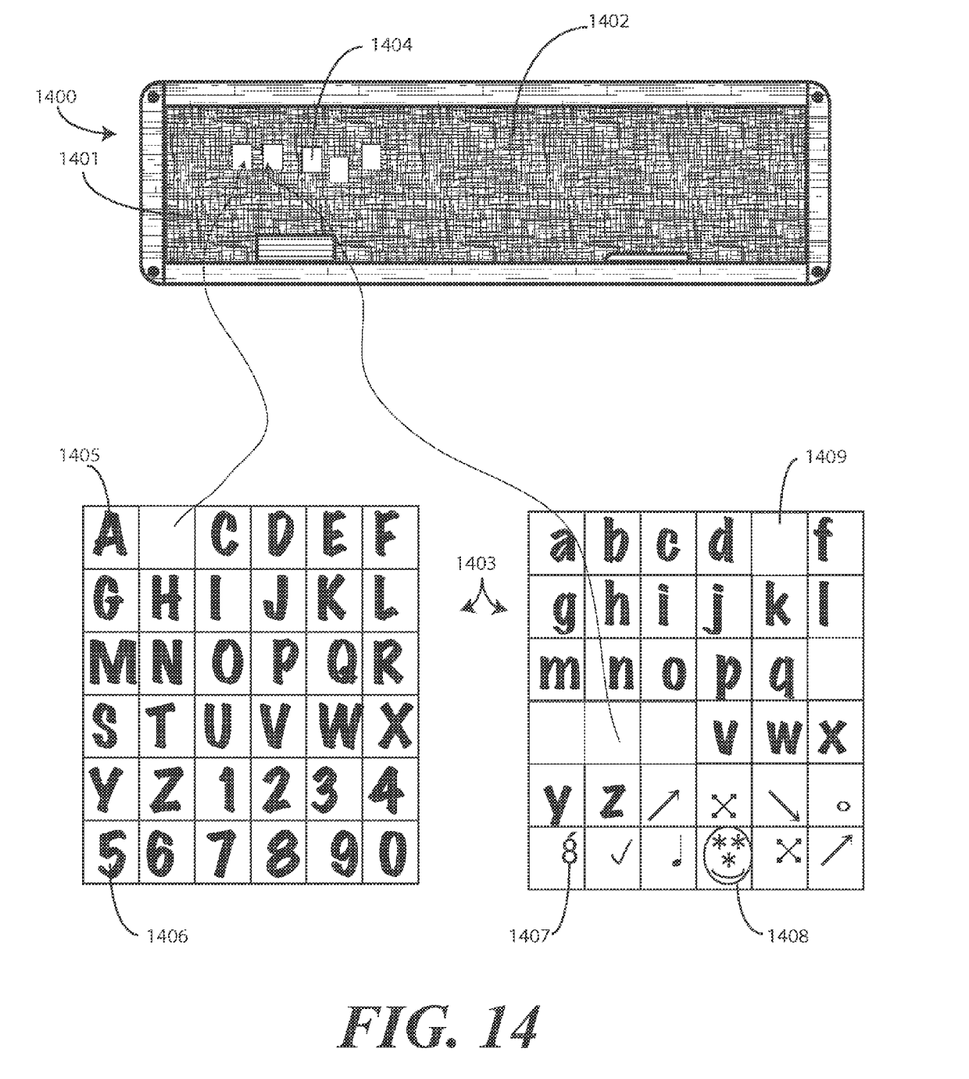
FIG. 14 illustrates an explanatory system in accordance with one or more embodiments of the disclosure.

Turning now to FIG. 14, illustrated therein is one explanatory system 1400 configured in accordance with one or more embodiments of the disclosure. The system 1400 includes a decorative bandage 1401 comprising one or more design elements defining a writing surface appearance 1402 on a major face of the decorative bandage 1401 and a plurality of stickers 1403. Each sticker is to adhere 1404 to the writing surface appearance 1402. As described with reference to FIG. 13 above, each sticker comprising one of a letter 1405, symbol 1407, character 1408, or number 1406 on a planar side of the each sticker. A user can selectively take stickers off a backing paper 1409 and apply them to the writing surface appearance 1402, which is configured as a blackboard appearance in this embodiment. Applying stickers to the writing surface appearance 1402 allows a user to customize the decorative bandage.

Figure 15:
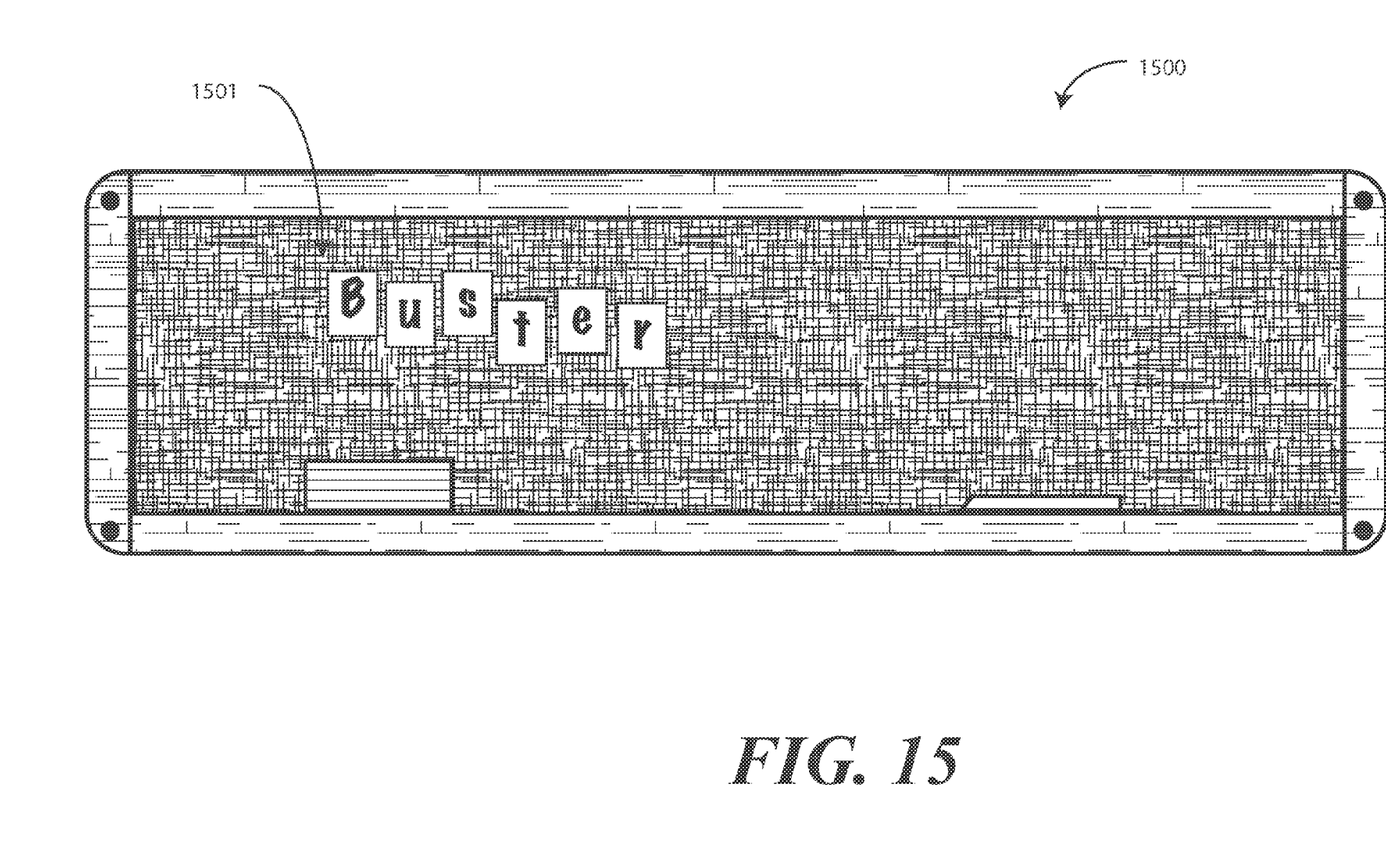
FIG. 15 illustrates another top plan view of another explanatory decorative bandage in accordance with one or more embodiments of the disclosure.

Turning now to FIG. 15, illustrated therein is one example of a customized bandage 1500. In the embodiment of FIG. 15, the writing surface appearance is customizable by disposing one or more stickers along the writing surface appearance 1501. A patient has personalized the customized bandage 1500 in this embodiment by attaching the name "Buster" to the writing surface appearance 1501.

Figure 16:
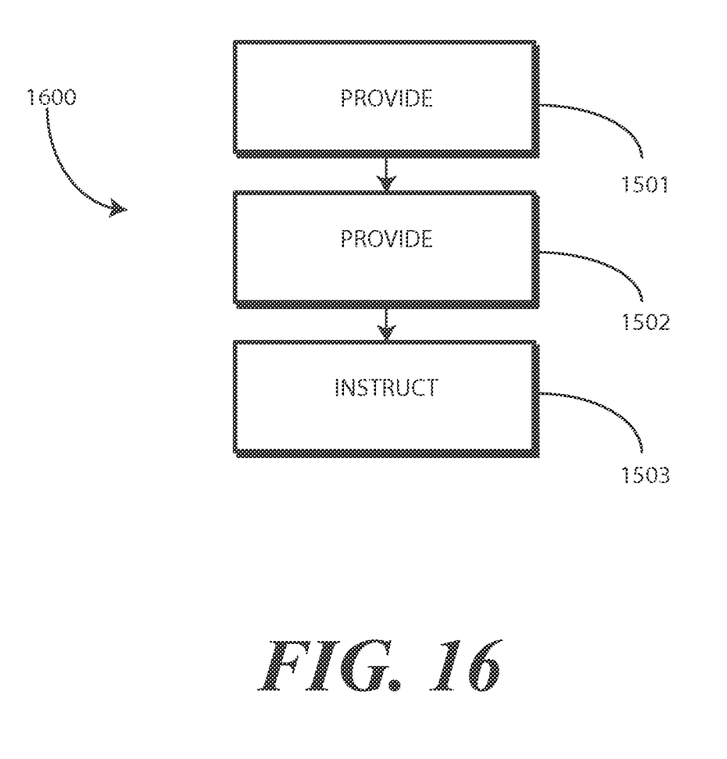
FIG. 16 illustrates an explanatory method in accordance with one or more embodiments of the disclosure.

Turning now to FIG. 16, illustrated therein is one explanatory method 1600 in accordance with one or more embodiments of the disclosure. At step 1601, the method 1600 provides one or more decorative bandages. At step 1601, each decorative bandage comprises one or more design elements defining a writing surface appearance on a major face of the decorative bandage.

At step 1602, the method provides a plurality of stickers. At step 1602, each sticker is configured to adhere to the writing surface appearance. At step 1602, each sticker comprises one of a letter, symbol, character, or number on a planar side of the each sticker. The characters can include cartoon characters, superheroes, and so forth.

At step 1603, the method 1600 instructs a user to customize an appearance of the one or more decorative bandages. In one embodiment, step 1603 instructs a user to customize a decorative bandage by applying one or more stickers to the writing surface appearance.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A decorative bandage, comprising:
   a backing layer defining a first major face and a second major face;
   an adhesive disposed along one of the first major face or the second major face;
   a pad disposed along the one of the first major face or the second major face;
   another of the first major face or the second major face comprising one or more design elements defining a writing surface appearance;
   the writing surface appearance comprising a blackboard appearance.

2. The decorative bandage of claim 1, the blackboard appearance comprising a black plane inscribed within a border defining a wood frame appearance.

3. The decorative bandage of claim 2, further comprising another design element defining a writing instrument appearance disposed along the blackboard appearance.

4. The decorative bandage of claim 3, the writing instrument appearance comprising a chalk stick appearance.

5. The system of claim 3, the writing instrument appearance comprising one of an ink pen appearance or a marker appearance.

6. The decorative bandage of claim 1, further comprising a sticker set, the sticker set comprising a plurality of stickers, each sticker having another adhesive to adhere to the writing surface appearance on a first side of the respective sticker and one of a letter, symbol, character, or number on a second side of the respective sticker.

7. The decorative bandage of claim 6, the plurality of stickers respectively comprising one of letters A through Z or numbers one through nine and zero disposed on respective second sides of the plurality of stickers.

8. The decorative bandage of claim 1, the backing layer comprising a thermoplastic material.

9. The decorative bandage of claim 8, the backing layer defining a length of between three and four inches, inclusive, and a width of between one and two inches, inclusive.

10. The decorative bandage of claim 1, the writing surface appearance printed on the another of the first major face or the second major face.

11. The decorative bandage of claim 1, the writing surface appearance comprising one or more letters, symbols, characters, numbers, or combinations thereof.

12. The decorative bandage of claim 1, the backing layer comprising a perforated backing layer.

\* \* \* \* \*